US012306297B2

(12) United States Patent
Sudo et al.

(10) Patent No.: US 12,306,297 B2
(45) Date of Patent: May 20, 2025

(54) ULTRASONIC PROBE (71) Applicant: Canon Medical Systems Corporation, Otawara (JP)

(72) Inventors: Masaaki Sudo, Otawara (JP); Takashi Takeuchi, Otawara (JP); Hiroyuki Shikata, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 491 days.

(21) Appl. No.: 17/388,416

(22) Filed: Jul. 29, 2021

(65) Prior Publication Data
US 2022/0035028 A1 Feb. 3, 2022

(30) Foreign Application Priority Data

Jul. 29, 2020 (JP) .................................. 2020-128158

(51) Int. Cl.
*G01S 15/89* (2006.01)
*A61B 8/00* (2006.01)
*B06B 1/06* (2006.01)

(52) U.S. Cl.
CPC ........ *G01S 15/8918* (2013.01); *A61B 8/4494* (2013.01); *B06B 1/0629* (2013.01); *G01S 15/8925* (2013.01); *G01S 15/8927* (2013.01); *A61B 8/4444* (2013.01)

(58) Field of Classification Search
CPC .................................................. G01S 15/8918
See application file for complete search history.

(56) References Cited

U.S. PATENT DOCUMENTS

| 8,091,428 | B2 * | 1/2012 | Takeuchi ............ G01S 15/8925 600/459 |
| 10,413,276 | B2 * | 9/2019 | Ona ..................... A61B 8/4494 |
| 11,510,648 | B2 * | 11/2022 | Shikata ................ G01S 7/5208 |
| 2006/0186765 | A1 | 8/2006 | Hashimoto |
| 2011/0181149 | A1 * | 7/2011 | Shikata ................ G10K 11/004 310/327 |

FOREIGN PATENT DOCUMENTS

| JP | 2006-102135 A | 4/2006 |
| JP | 2006-288420 A | 10/2006 |
| JP | 2009-200838 A | 9/2009 |
| JP | 2017/527375 A | 9/2017 |
| JP | 2019-097774 A | 6/2019 |

OTHER PUBLICATIONS

Japanese Office Action issued Feb. 15, 2024 in Japanese Patent Application No. 2020-128158, 3 pages.
Japanese Office Action issued Feb. 13, 2024 in Japanese Patent Application No. 2020-128158, 3 pages.
Japanese Office Action issued Jul. 23, 2024 in Japanese Patent Application No. 2020-128158, 3 pages.

* cited by examiner

*Primary Examiner* — Ryan D Walsh
(74) *Attorney, Agent, or Firm* — Oblon, McClelland, Maier & Neustadt, L.L.P.

(57) ABSTRACT

According to one embodiment, an ultrasonic probe includes a plurality of ultrasonic transducers, a first substrate, and a plurality of electronic circuit modules. The plurality of ultrasonic transducers are equally spaced and aligned at least in one direction. The first substrate to which the ultrasonic transducers are coupled. The plurality of electronic circuit modules provided at predetermined intervals one the first substrate and coupled to the first substrate.

10 Claims, 11 Drawing Sheets

ULTRASONIC PROBE

CROSS-REFERENCE TO RELATED APPLICATIONS

This application is based upon and claims the benefit of priority from Japanese. Patent Application No. 2020-128158, filed Jul. 29, 2020, the entire contents of which are incorporated herein by reference.

FIELD

Embodiments described herein relate generally to an ultrasonic probe.

BACKGROUND

An ultrasonic diagnostic apparatus forms an image of an inside of a target object (patient) by transmitting ultrasonic waves to the target and receiving reflected waves (echo) from the inside of the target. In recent years, two-dimensional array ultrasonic probes (also referred to as "two-dimensional array probes") have mainly been employed. A two-dimensional array probe includes a large number of ultrasonic transducers (also simply referred to as "elements") arranged in a two-dimensional lattice, which makes it difficult to control the ultrasonic transmission and reception of ultrasonic waves by driving all the main elements directly from the main body of the ultrasonic diagnostic apparatus. For this reason, the ultrasonic probe is provided with an IC (application specific integrated circuit or ASIC) specifically configured to perform an add operation for partially delaying individual elements.

Underneath the lattice of the two-dimensionally arranged elements are a plurality of electronic circuit modules that are coupled to each other with no space in-between, where a certain number of elements (or sub-arrays) constitute one module. Each electronic circuit module includes a backing material, a flexible printed circuit (FPC), and an ASIC. In each electronic circuit module, the FPC is folded so as to surround the backing material, and the wirings are pulled out. The pulled-out wirings are coupled to the ASIC. Such coupling can realize an ultrasonic probe having a large-scale array structure, in which the coupling of the elements is distributed to different electronic circuit modules, and the electronic circuit modules are stacked in one direction (e.g., elevation direction).

In order to tightly couple the electronic circuit modules in the above coupling and fit the modules to the substrate on which the elements are arranged, the electronic circuit modules need to be prepared with a high degree of precision. It is difficult, however, to avoid distortion and deformation of the FPC at the time of folding with the above coupling method, as a result of which the assembling precision tends to be lowered in the production of an ultrasonic probe.

DETAILED DESCRIPTION

In general, according to one embodiment, an ultrasonic probe includes a plurality of ultrasonic transducers, a first substrate, and a plurality of electronic circuit modules. The plurality of ultrasonic transducers are equally spaced and aligned at least in one direction. The first substrate to which the ultrasonic transducers are coupled. The plurality of electronic circuit modules provided at predetermined intervals one the first substrate and coupled to the first substrate.

The embodiments will be described below with reference to the drawings.

First Embodiment

Figure 1:
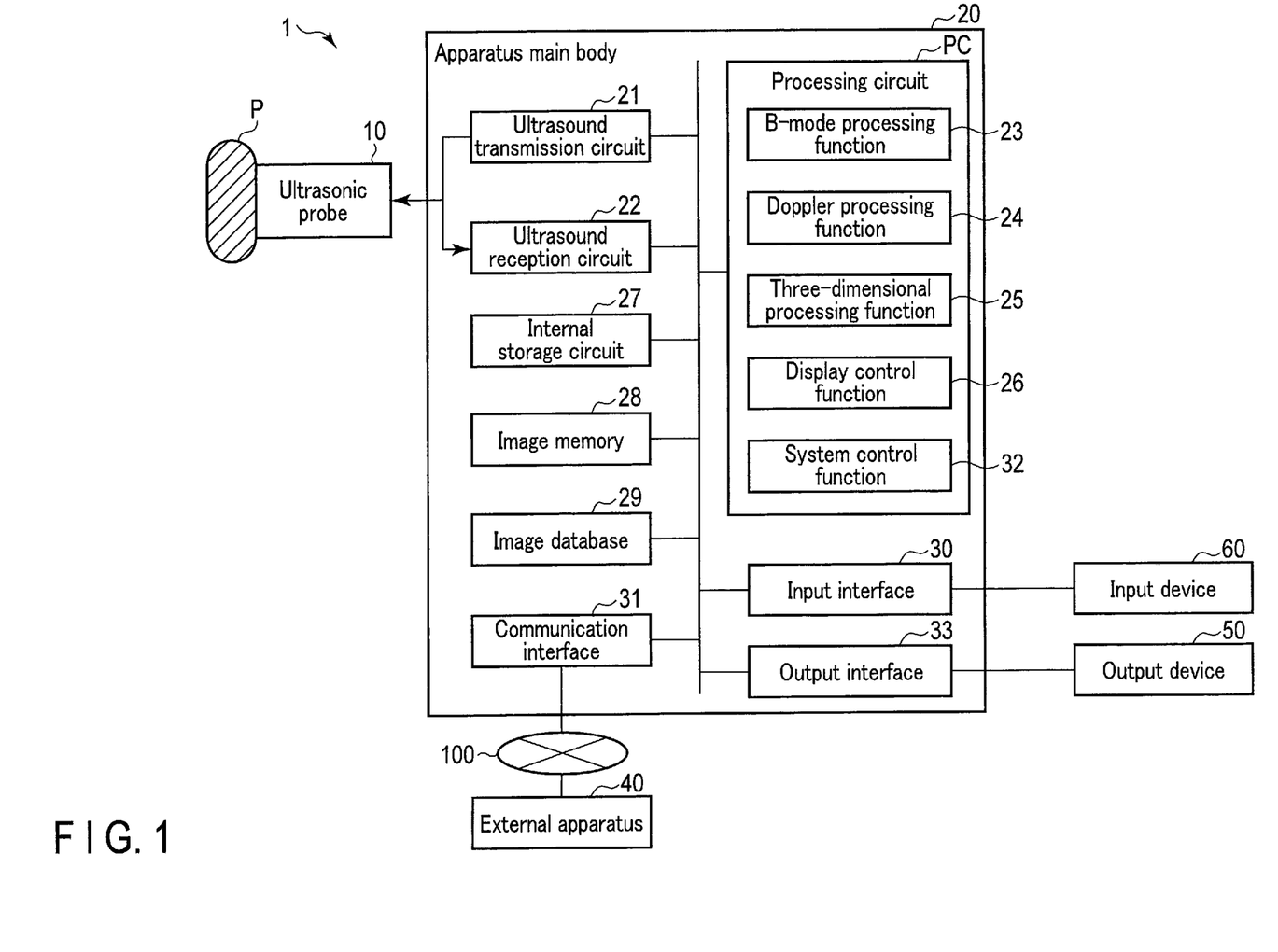
FIG. 1 is a diagram for showing an exemplary configuration of an ultrasonic diagnostic apparatus according to the first embodiment.

FIG. 1 is a block diagram showing an exemplary configuration of an ultrasonic diagnostic apparatus according to the first embodiment. For instance, as illustrated in FIG. 1, an ultrasonic diagnostic apparatus 1 according to the first embodiment includes an ultrasonic probe 10 and an apparatus main body 20. The apparatus main body 20 is coupled to an external apparatus 40 via a network 100. The apparatus main body 20 is also coupled to an output device 50 and an input device 60.

The ultrasonic probe 10 includes a plurality of ultrasonic transducers (which may be simply referred to as "elements"), a matching layer on the elements, a backing material (back side acoustic load material) for preventing the ultrasound waves from propagating backward from the elements, and the like. The ultrasonic probe 10 is detachably coupled to the apparatus main body 20. The ultrasonic probe 10 according to the first embodiment may be a two-dimensional array probe in which a plurality of ultrasonic transducers are aligned, for example in a first element alignment direction (elevation direction) and a second element alignment direction (azimuth direction). The ultrasonic probe 10 will be described later in detail.

The apparatus main body 20 in FIG. 1 is configured to generate an ultrasonic image based on a reflection wave signal received by the ultrasonic probe 10. The apparatus main body 20 includes an ultrasound transmission circuit 21, an ultrasound reception circuit 22, a processing circuit PC, an internal storage circuit 27, an image memory (cine-memory), an image database 29, an input interface 30, a communication interface 31, and an output interface 33, as illustrated in FIG. 1.

The ultrasound transmission circuit 21 is a processor that supplies a drive signal to the ultrasonic probe 10. The ultrasound transmission circuit 21 is realized by, for example, a trigger generation circuit, a delay circuit, and a pulser circuit. The trigger generating circuit repeatedly generates a rate pulse for forming a transmission ultrasonic wave at a predetermined rate frequency. The delay circuit supplies a transmission delay time for each element to each rate pulse generated by the trigger generation circuit, where this delay time is required to converge the ultrasound wave generated by the ultrasonic probe 10 into a beam and to determine the transmission directivity. The pulser circuit applies a drive signal (drive pulse) to the ultrasonic probe 10 at a timing based on the rate pulse. The delay circuit varies the delay times that are to be supplied to the rate pulses so that the transmission direction from the surface of the element can be freely adjusted.

The ultrasound reception circuit 22 is a processor that performs various kinds of processing on the reflection wave signal received by the ultrasonic probe 10 to generate a reception signal. The ultrasound reception circuit 22 generates a reception signal corresponding to the reflection wave signal of an ultrasound wave acquired by the ultrasonic probe 10. In particular, the ultrasound reception circuit 22 is realized, for example, by a preamplifier, an A/D converter, a demodulator, and a beam former. The preamplifier performs gain correction processing by amplifying the reflection wave signal received by the ultrasonic probe 10 for each channel. The A/D converter converts the gain-corrected reflection wave signal to a digital signal. The demodulator demodulates this digital signal. The beam former supplies, to the demodulated digital signal, a delay time required to determine the reception directivity, and adds the digital signals to which the delay time is supplied. Through the addition processing by the beam former, a reception signal is generated in which a reflection component from the direction corresponding to the reception directivity is emphasized.

The processing circuit PC may be a processor that serves as the center of the ultrasonic diagnostic apparatus 1. The processing circuit PC implements the program stored in the internal storage circuit 27, thereby realizing the functions corresponding to the program. The processing circuit PC may have a B-mode processing function 23, a Doppler processing function 24, a three-dimensional processing function 25, a display control function 26, and a system control function 32. The functions implemented by the processing circuit PC may be installed as a program as described above, or a hardware circuit specifically designed to implement each function may be incorporated into the processing circuit PC or the apparatus main body 20.

The B-mode processing function 23 is configured to generate B-mode data based on the reception signal received from the ultrasound reception circuit 22. The processing circuit PC, when implementing the B-mode processing function 23, executes envelope detection processing, logarithmic amplification processing and the like upon the reception signal received from the ultrasound reception circuit 22 to generate data (hereinafter, "B-mode data") that expresses the signal intensity with luminance. The generated B-mode data is stored as B-mode raw data on two-dimensional ultrasound scanning lines (rasters) in a raw data memory (not shown). Alternatively, the B-mode raw data may be stored in the internal storage circuit 27 as described later.

The Doppler processing function 24 is configured to generate a Doppler waveform and Doppler data based on the reception signal received from the ultrasound reception circuit 22. The processing circuit PC, when implementing the Doppler processing function 24, extracts a bloodstream signal from the reception signal, generates a Doppler waveform from the extracted bloodstream signal, and generates data (hereinafter, "Doppler data") including an average speed, dispersion, and power, which are extracted from the bloodstream signal with respect to multiple points.

The three-dimensional processing function 25 is configured to generate two-dimensional image data or three-dimensional image data (which may also be referred to as volume data), based on the data generated by the B-mode processing function 23 and Doppler processing function 24. The processing circuit PC configured to implement the three-dimensional processing function 25 executes a raw-pixel conversion so as to generate two-dimensional image data constituted by pixels.

Furthermore, the processing circuit PC, when implementing the three-dimensional processing function 25, executes a raw-voxel conversion upon the B-mode raw data stored in the raw data memory. This conversion includes interpolation processing, incorporating the positional information of space. In this manner, volume data constituted by multiple voxels of a desired range can be generated. Then, the processing circuit PC implements rendering processing upon the generated volume data to generate rendering image data. Hereinafter, B-mode raw data, two-dimensional image data, volume data and rendering image data may be altogether referred to as ultrasonic data.

The display control function 26 is configured to execute various types of processing including dynamic range, luminance (brightness), contrast, γ curve correction, and RGB conversion upon various types of image data generated by the three-dimensional processing function 25, and display the resultant image data on the output device 50. The processing circuit PC configured to implement the display control function 26 may generate a graphical user interface (GUI) to allow the operator to input various commands through the input interface 30, and display the GUI on the output device 50.

The system control function 32 is for controlling the operations of the ultrasonic diagnostic apparatus 1 overall. For instance, with the system control function 32, the processing circuit PC generates row delay data for the two-dimensionally aligned elements. The row delay data is determined for each row of elements in each direction, for example when a two-dimensional array probe including a plurality of ultrasonic transducers aligned in the first element alignment direction and second element alignment direction is adopted. The processing circuit PC further generates delay data for each sub-array in relation to the delay of the overall system, and transmits the generated delay data as an analog signal to the ultrasound transmission circuit 21.

The internal storage circuit 27 may include a processor readable storage medium such as a magnetic storage medium, an optical storage medium, or a semiconductor memory. The internal storage circuit 27 stores therein programs for realizing ultrasonic transmission/reception, for image processing, and for display processing, as well as various types of data. These programs and data may be stored in advance in the internal storage circuit 27, or may be stored in a non-transitory storage medium so that the medium can be distributed and the programs and data can be read from the medium to be installed in the internal storage circuit 27.

The internal storage circuit 27 further stores the B-mode image data, two-dimensional image data, volume data, rendered image data generated by the processing circuit PC, and the like in accordance with a storing operation input by way of the input interface 30. The internal storage circuit 27 may also transfer the stored data to an external apparatus 40 via the communication interface 31.

The internal storage circuit 27 may be a driving device that reads and writes various types of information with respect to a portable storage medium such as a CD-ROM drive, DVD drive, or flash memory. The internal storage circuit 27 may write the stored data into a portable storage medium so that the data can be stored into an external apparatus 40 by way of the portable storage medium.

The image memory 28 may include a storage medium that can be read by a processor such as a magnetic storage medium, an optical storage medium or a semiconductor memory. The image memory 28 stores therein image data corresponding to a plurality of frames immediately before a freeze operation that is input via the input interface 30. The image data stored in the image memory 28 may be sequentially displayed (as moving images).

The image database 29 may store the image data transferred from the external apparatus 40. For instance, the image database 29 receives and stores past medical image data acquired at past examinations of a target patient and stored in the external apparatus 40. The past medical image data may include ultrasonic image data, computed tomography (CT) image data, MR image data, positron emission tomography (PET)-CT image data, PET-MR image data, and X-ray image data.

The image database 29 may read image data from a storage medium such as an MO, CD-R, and DVD, and store the targeted image data.

The input interface 30 receives various commands from the operator via the input device GO. The input device GO may include a mouse, a keyboard, panel switches, slider switches, a track ball, a rotary encoder, an operation panel, a touch command screen (TCS), and the like. The input interface 30 is coupled to the processing circuit PC, for example, via a bus. The input interface 30 converts an operation command input by the operator to an electric signal, and outputs the electric signal to the processing circuit PC. The input interface 30 is not limited to a component that is coupled to a physical component for performing operations such as a mouse and keyboard. Examples of the input interface 30 include an electric signal processing circuit configured to receive an electric signal corresponding to an operation command that is input from an external input device provided separately from the ultrasonic diagnostic apparatus 1 and to output this electric signal to the processing circuit PC.

The communication interface 31 is coupled to the external apparatus 40, for example, via the network 100, to perform data communications with the external apparatus 40. The external apparatus 40 may be a database for a picture archiving and communication system (PACS) that manages the data of various medical images, or a database for an electronic medical chart system that manages electronic charts to which medical images are attached. The external apparatus 40 may be any medical image diagnostic apparatus such as an X-ray CT apparatus, a magnetic resonance imaging (MRI) apparatus, a nuclear medicine diagnostic apparatus, and an X-ray diagnostic apparatus, that is, any apparatus excluding the ultrasonic diagnostic apparatus 1 according to the first embodiment. Any communication standard may be adopted for communications with the external apparatus 40, examples of which include digital imaging and communication in medicine (DICOM).

The output interface 33 is an interface for displaying display image data received from the processing circuit PC on the output device 50. The output device 50 includes a liquid crystal display, an organic EL display, an LED display, a plasma display, a CRT display or any other display. The output device 50 may be a touch-panel display that can also serve as the input device 60. The output interface 33 may be coupled to the processing circuit PC via a bus to output to the output device 50 an electric signal received from the processing circuit PC.

The basic configuration of the ultrasonic diagnostic apparatus 1 according to the first embodiment has been explained. Next, the configuration of the ultrasonic probe 10 according to the first embodiment will be explained with reference to FIGS. 2 and 3.

Figure 2:
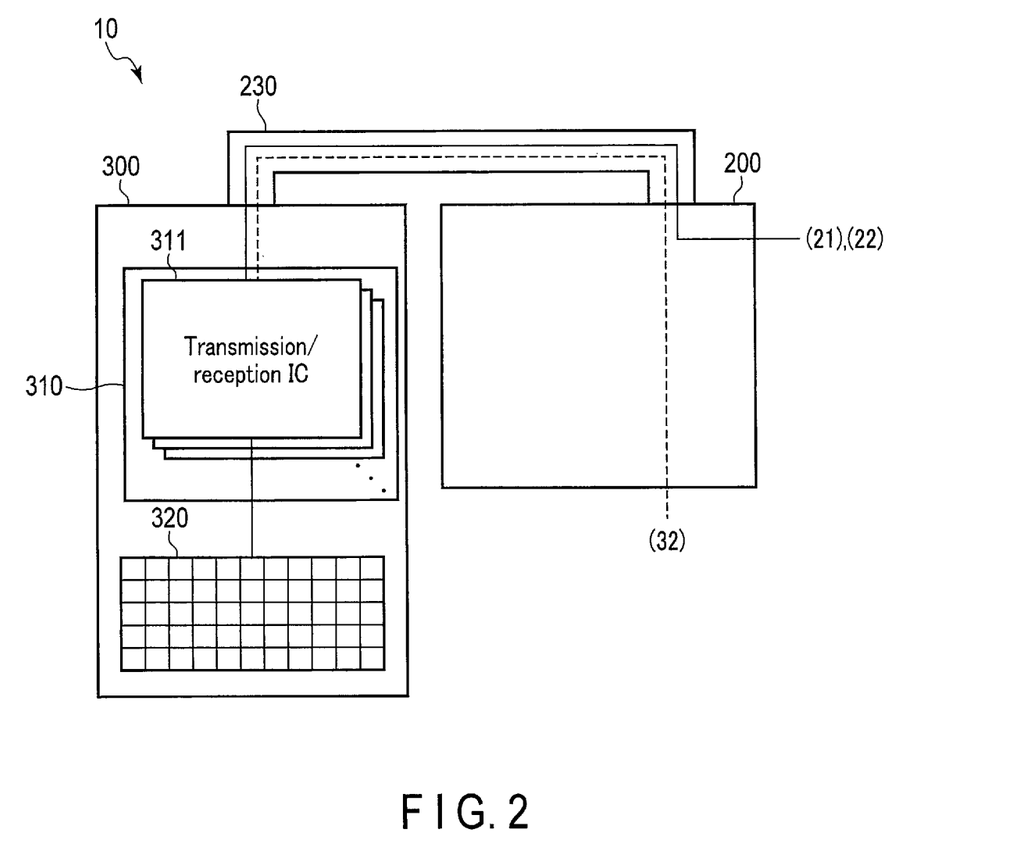
FIG. 2 is a block diagram for showing an exemplary functional configuration of an ultrasonic probe according to the first embodiment.

FIG. 2 is a block diagram for showing an exemplary functional configuration of an ultrasonic probe according to the first embodiment. The ultrasonic probe 10 according to the first embodiment includes a coupler 200 (also referred to as a "pod"), a cable 230, and a probe main body 300 (also referred to as a "head"), as illustrated in FIG. 2. The coupler 200 is coupled to the apparatus main body 20. The cable 230 couples the coupler 200 to the probe main body 300. The probe main body 300 exchanges control signals and data with the apparatus main body 20 via the cable 230 and coupler 200.

The probe main body 300 includes an electronic circuit unit 310 and a plurality of ultrasonic transducers 320. The electronic circuit unit 310 includes a plurality of transmission/reception ICs 311 (transmission/reception circuits). Each of the transmission/reception ICs 311 receives row delay data via a not-shown communication control circuit from a processing circuit PC implementing the system control function 32 of the apparatus main body (hereinafter simply referred to as a "processing circuit PC"), and also receives a drive signal from the ultrasound transmission circuit 21. Based on the row delay data and drive signal, each of the transmission/reception ICs 311 sets a delay amount of elements for the corresponding sub-array, and controls the transmission and reception of ultrasound waves at a certain timing. A storage circuit may be provided in the coupler 200 so as to store the row delay data received from the processing circuit PC.

The ultrasonic transducers 320 are equally spaced from each other and aligned at least in one direction. In particular, the ultrasonic transducers 320 are arranged into a two-dimensional matrix, at regular intervals in two mutually perpendicular directions. An element delay amount for each of the ultrasonic transducers 320 is determined by the transmission/reception IC 311, and the ultrasound wave based on the drive signal is transmitted to a subject P at a timing corresponding to the delay amount. The ultrasonic transducers may also be referred to as acoustic transduction elements.

When an ultrasound wave is transmitted from the ultrasonic probe 10 to the subject P, the transmitted ultrasound wave is sequentially reflected on the acoustic impedance discontinuous surface of the body tissue of the subject P, and is received as a reflection wave by the ultrasonic transducers 320. The amplitude of the received reflection wave depends on the difference in acoustic impedance on the discontinuous surface on which the ultrasound wave is reflected. If the transmitted ultrasonic pulse is reflected from the surface of a moving bloodstream or cardiac wall, the frequency of the reflection wave is shifted due to the Doppler effect, with the shift depending on the velocity component in the ultrasound wave transmission direction of the moving object. The ultrasonic probe 10 receives the reflection wave from the subject P and converts it to an electric signal to transmit to the apparatus main body 20.

Figure 3:
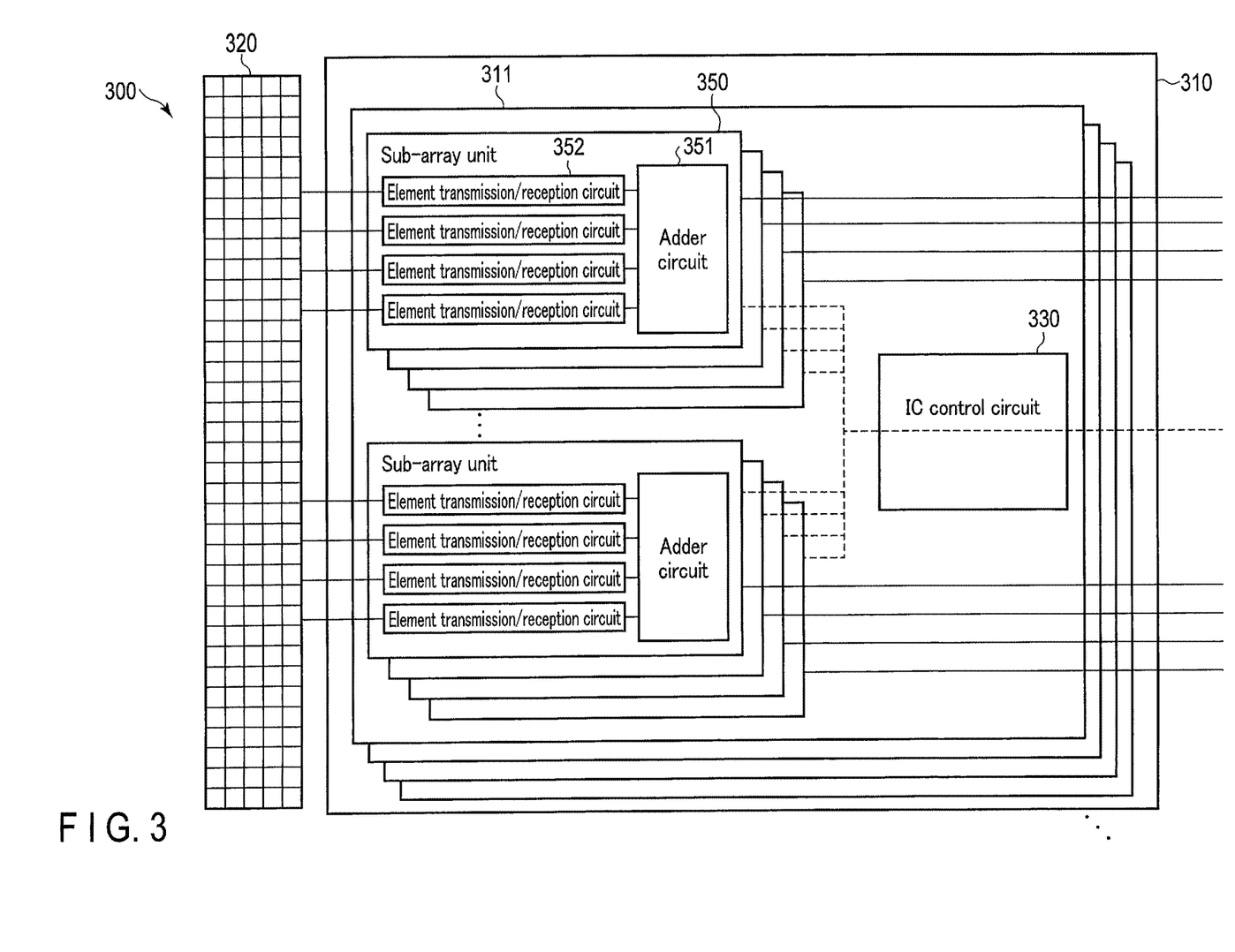
FIG. 3 is a block diagram for showing an exemplary configuration of a probe main body according to the first embodiment.

FIG. 3 is a block diagram showing an exemplary configuration of the probe main body according to the first embodiment. The detailed configuration of the transmission/reception ICs 311 in the electronic circuit unit 310 of the probe main body 300 is illustrated in FIG. 3. For instance, as illustrated in FIG. 3, the transmission/reception IC 311 includes an IC control circuit 330 and a plurality of sub-array units 350.

The IC control circuit 330 calculates a delay amount for each element of each sub-array from the row delay data acquired from the communication control circuit of the coupler 200, and sets the delay amount to each of the sub-array units 350.

Each sub-array unit 350 includes an adder circuit 351 and a plurality of element transmission/reception circuits 352. One element transmission/reception circuit 352 is provided for each channel. The element transmission/reception circuit 352 includes a delay circuit, a transmission amplification circuit, a transmission reception separation circuit, and a reception amplification circuit.

The adder circuit 351 adds reception signals that have been subjected to the delay processing by the delay circuits of the element transmission/reception circuits 352. The delay circuit of each element transmission/reception circuit 352 receives a delay amount from the IC control circuit 330, a drive signal from the ultrasound transmission circuit 21, and a reception signal of an ultrasonic transducer from the reception amplification circuit, and sets a delay amount to a transmission/reception signal. The transmission amplification circuit of the element transmission/reception circuit 352 receives a drive signal from the delay circuit, and amplifies the drive signal. The transmission reception separation circuit of the element transmission/reception circuit 352 separates the drive signal, which relates to the transmission, from an echo signal received by the elements. The reception amplification circuit of the element transmission/reception circuit 352 amplifies an echo signal from the transmission reception separation circuit, and amplifies the echo signal.

Each of the sub-array units 350 receives a drive signal from the ultrasound transmission circuit 21, and a delay amount from the IC control circuit 330. Based on the drive signal and delay amount, the sub-array unit 350 controls the timing of the ultrasonic transmission/reception of the elements in the corresponding sub-array.

The functional configuration of the ultrasonic probe according to the first embodiment has been explained. Next, the physical configuration of the ultrasonic probe 10 according to the first embodiment will be described.

Figure 4:
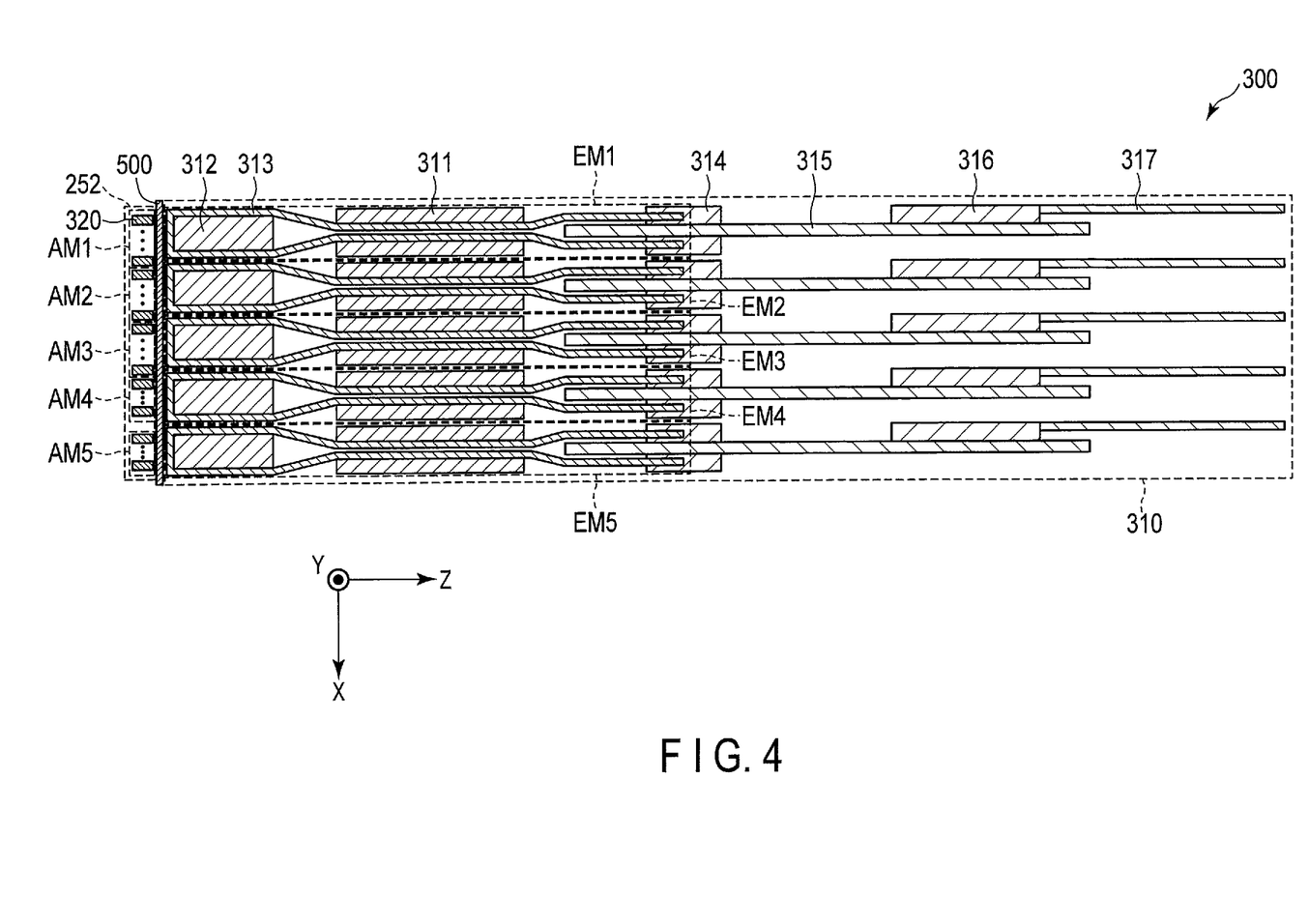
FIG. 4 is an exemplary cross sectional view of the probe main body according to the first embodiment.
Figure 5:
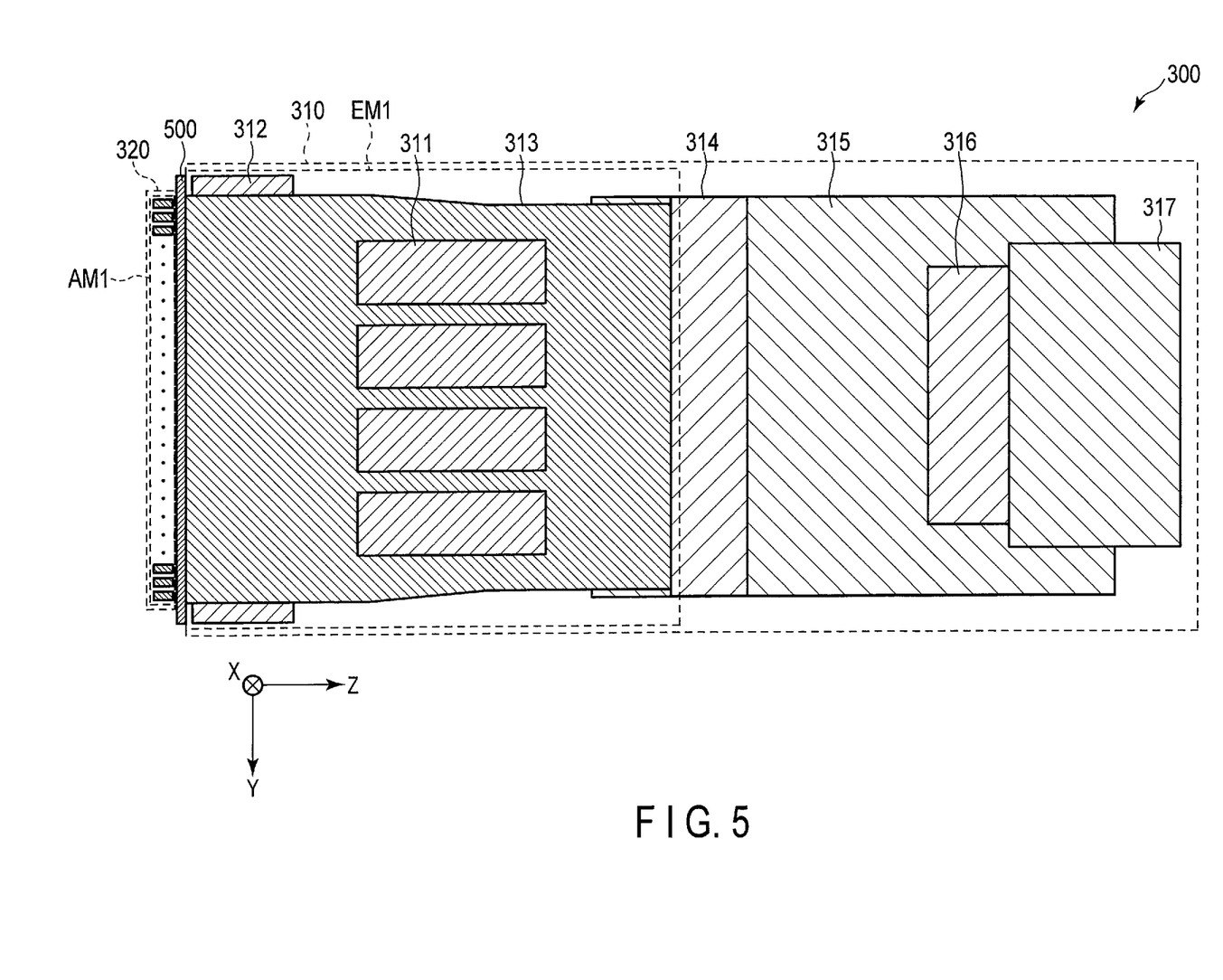
FIG. 5 is an exemplary top view of the probe main body according to the first embodiment.

FIG. 4 is an exemplary cross sectional view of the probe main body according to the first embodiment. FIG. 5 is an exemplary top view of the probe main body according to the first embodiment. In the following description, the axis extending in the first direction, or in other words in the elevation direction, will be determined to be an X-axis, while the axis extending in the second direction, or in other words in the azimuth direction, will be determined to be a Y-axis, which is orthogonal to the X-axis, as illustrated in FIGS. 4 and 5. The axis perpendicular to the XY plane will be determined to be a Z-axis.

As illustrated in FIGS. 4 and 5, the probe main body 300 of the ultrasonic probe 10 according to the first embodiment includes a plurality of ultrasonic transducers 320, a base substrate 500, and an electronic circuit unit 310.

Figure 6:
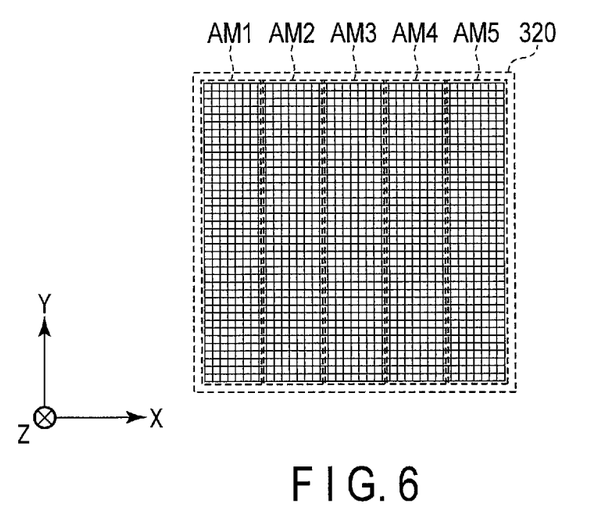
FIG. 6 is a diagram showing a plurality of ultrasonic transducers according to the first embodiment when viewed from the ultrasonic emission direction.

The ultrasonic transducers 320 are two-dimensionally aligned along the X-axis (elevation direction) and Y-axis (azimuth direction). The ultrasonic transducers 320 are divided into transducer modules, each of which includes a predetermined number of elements. FIG. 6 is a diagram showing a plurality of ultrasonic transducers according to the first embodiment when viewed from the ultrasonic emission direction. For instance, the ultrasonic transducers 320 are divided into five transducer modules, namely transducer modules AM1, AM2, AM3, AM4, and AM5, as illustrated in FIGS. 4 and 6. Underneath the ultrasonic transducers 320 (on the surface in the positive direction side of the Z-axis) is provided a base substrate 500.

The base substrate 500 may be an FPC or the like. The base substrate 500 may be a flexible wiring board. The base substrate 500 is provided between the ultrasonic transducers 320 and the electronic circuit unit 310. The base substrate 500 is a non-divided structure, supporting the ultrasonic transducers 320. The base substrate 500 is a board with the two surfaces having copper-foil wiring patterns. The base substrate 500 electrically couples the ultrasonic transducers 320 to the electronic circuit unit 310 for each module. Because of the base substrate being an FPC, the radiation of an ultrasound wave toward the back side of the elements effectively reaches the back side and then decays. As a result, an adverse influence such as poor convergence can be avoided on a generated image. The base substrate 500 may be constituted by a multi-layer rigid board.

The electronic circuit unit 310 may include electronic circuit modules EM1, EM2, EM3, EM4, and EM5. The electronic circuit modules EM1, EM2, EM3, EM4, and EM5 are electrically coupled to the transducer modules AM1, AM2, AM3, AM4, and AM5 via the base substrate 500. The electronic circuit modules EM1, EM2, EM3, EM4, and EM5 are aligned on the opposite surface of the base substrate 500 in the thickness direction of the base substrate 500 with respect to the surface on which the transducer modules AM1, AM2, AM3, AM4, and AM5 are aligned. The electronic circuit modules EM1, EM2, EM3, EM4, and EM5 are stacked in the X-axis direction (elevation direction). The number of electronic circuit modules in the electronic circuit unit 310 is not limited to five. The number of electronic circuit modules may be increased or reduced in accordance with the number of ultrasonic transducers 320 (i.e., the scale of the ultrasonic transducer array constituted by a plurality of ultrasonic transducers 320), or the number of transducer modules.

Each of the electronic circuit modules EM1, EM2, EM3, EM4, and EM5 includes a backing material 312 and an FPC 313. The physical configuration of an electronic circuit module will be described below. The FPC 313 may also be referred to as a flexible wiring board.

The backing material 312 is configured to prevent ultrasound waves from propagating backward (i.e., in the positive direction of the Z-axis) with respect to the acoustic radiation direction of the ultrasonic transducers 320. Part of the surface of the backing material 312 has the FPC 313 adhered thereto.

The FPC 313 is adhered to part of the backing material 312. In particular, the FPC 313 is folded in such a manner as to be approximately in contact with the surface (first surface) of the backing material 312 on the negative direction side of the Z-axis, the surface thereof on the positive direction side of the X-axis, and the surface thereof on the negative direction side of the X-axis, where the FPC 313 is adhered at least to the first surface. The surface of the backing material 312 on the negative direction side of the Z-axis is parallel to the base substrate 500. As a result, the FPC 313 has a two-layer structure with respect to the direction of the X-axis.

The width of the backing material 312 in the elevation direction is designed to be smaller than the module pitch in consideration of the widths of the two FPCs 313 between two adjacent electronic circuit modules and also of the warpage and distortion of the folded FPCs 313. The module pitch corresponds, for example, to the width of a transducer module in the X-axis direction. The electronic circuit modules are arranged at predetermined intervals, keeping a predetermined distance from an adjacent electronic circuit module. A predetermined interval may be a distance that is large enough so that the two FPCs 313 between any two adjacent electronic circuit modules will not be in contact with each other.

Each of the electronic circuit modules EM1, EM2, EM3, EM4, and EM5 includes, for example, eight transmission/reception ICs 311. The electronic circuit unit 310 therefore includes forty transmission/reception ICs in total.

The eight transmission/reception ICs 311 are directly mounted, for example by a Chip-On-Film (COF) technique, in such a manner as to sandwich the two-layered FPC 313 in the X-axis direction. In particular, in the electronic circuit module EM1, four transmission/reception ICs 311 are directly mounted on the FPC 313 on the negative direction side of the X-axis, as illustrated in FIG. 5. Similarly, four transmission/reception ICs 311 are directly mounted on the FPC 313 on the positive direction side of the X-axis in the electronic circuit module EM1. The transmission/reception ICs 311 being directly mounted on the. FPC 313 means that the electrode pads of the FPC 313 and input pins on the ultrasonic transducer side of the transmission/reception IC 311 are wired by FPC wiring. This can reduce the number of output pins on the apparatus main body side of the transmission/reception IC 311. Thus, for a connection with other control substrates, a commonly known coupling method such as FPC-connector coupling may be adopted.

Furthermore, as illustrated in FIGS. 4 and 5, the FPC 313 of the electronic circuit module EM1 is coupled to an FPC connector 314. The FPC connector 314 is coupled to the cable 315. The cable 315 is coupled to the cable connector 316. The cable connector 316 is coupled to the cable 317. The cable 317, which serves as part of the cable 230 in FIG. 2, is coupled to the coupler 200. The same arrangement is made for other electronic circuit modules.

The reflection wave signals generated by the ultrasonic transducers 320 in the transducer modules are transferred to the apparatus main body 20 by way of the FPC 313, FPC connector 314, cable 315, cable connector 316, and cable 317 of the electronic circuit modules respectively corresponding to the transducer modules.

Here, space is created between the FPCs 313 and the base substrate 500 immediately under the ultrasonic transducers 320. This space tends to hamper the effective acoustic radiation to the back surface (the surface on the positive direction side of the Z-axis) of the base substrate 500, which deteriorates the convergence of the waveform. In order to prevent this, the space between the base substrate 500 and the FPCs 313 is filled with a non-conductive resin such as epoxy resin. After filling the space with the non-conductive resin, this resin is cured under pressure, thereby establishing a pressurized connection between the base substrate 500 and the FPCs 313.

As a result, the filling non-conductive resin serves as a support member that structurally supports the ultrasonic transducers 320, enhancing the reliability of the ultrasonic probe 10.

By stacking the electronic circuit modules EM1, EM2, EM3, EM4, and EM5 in the direction of the X-axis (elevation direction) in the above described manner, the number of coupled transmission/reception ICs 311 can be increased.

The physical configuration of the ultrasonic probe 10 according to the first embodiment has been explained. Next, the configuration of the probe main body according to the first embodiment will be explained in detail.

Figure 7:
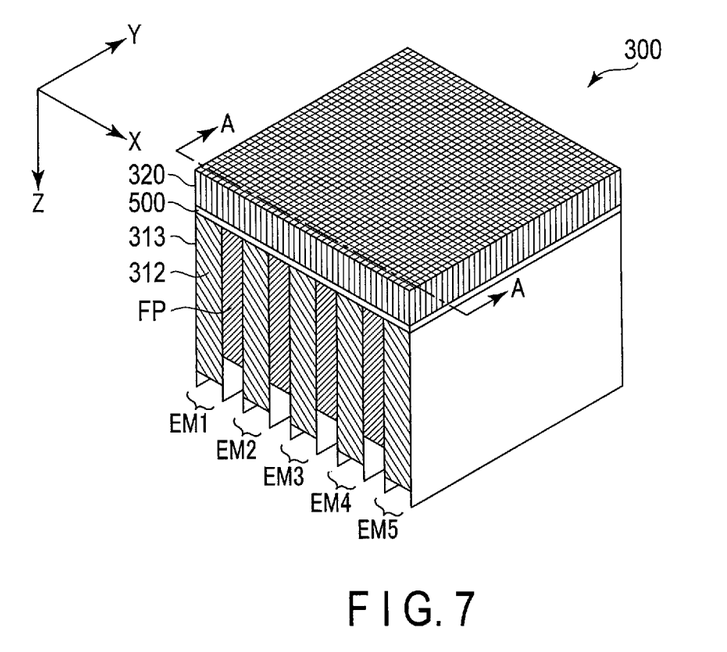
FIG. 7 is a perspective diagram for showing the configuration of the probe main body according to the first embodiment.

FIG. 7 is a perspective diagram showing the configuration of the probe main body according to the first embodiment. The electronic circuit modules are arranged at predetermined intervals, as illustrated in FIG. 7. A filler FP is provided between any two adjacent electronic circuit modules. For the filler FP, all or part of the materials used for the backing material, or an epoxy resin, may be adopted. The filler FP between the electronic circuit modules enhances the strength of the probe main body.

Figure 8:
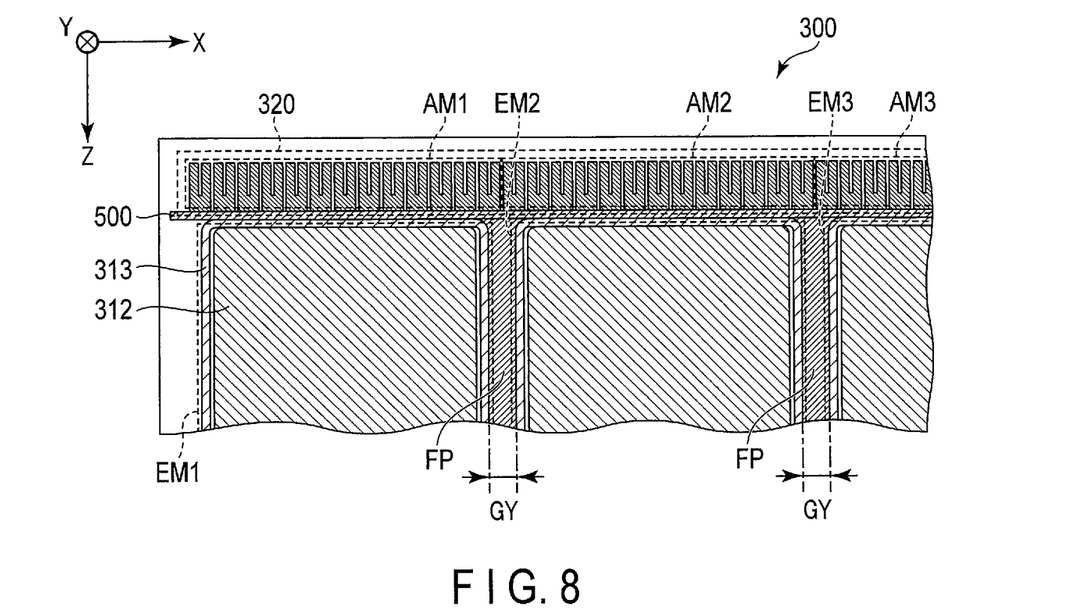
FIG. 8 is a cross-sectional view of the configuration of FIG. 7 taken along A-A in the Z-axis direction.

FIG. 8 is a cross-sectional view of the configuration of FIG. 7 taken along A-A in the Z-axis direction, where A-A is a line extending in the elevation direction (X-axis direction). The cross section of FIG. 8 is parallel to the XZ plane. The following explanation mainly deals with the configuration of the structure between the electronic circuit module EM1 and the electronic circuit module EM2. This configuration applies to the structures between the electronic circuit modules EM2 and EM3, between the electronic circuit modules EM3 and EM4, and between the electronic circuit modules EM4 and EM5.

In FIG. 8, the transducer module AM1 and transducer module AM2 are electrically coupled to the electronic circuit module EM1 and electronic circuit module EM2, respectively, by way of the base substrate 500. A predetermined space (gap GY) is provided between the electronic circuit module EM1 and electronic circuit module EM2, which are both attached to the base substrate 500. The width of the gap GY is determined in consideration of dimensional deviations such as warpage and distortion of the FPC 313 when folding the FPC 313 in the Z-axis direction. For instance, if it is assumed that a dimensional deviation of 0.01 mm appears in one FPC 313 due to folding, the aligned electronic circuit modules will not contact each other if the distance between two adjacent FPCs 313 is 0.02 mm or larger. A filler FP is provided in the gap GY.

A plurality of electrode pads are provided on the front surface of the base substrate 500 at intervals corresponding to the inter-element pitch of the ultrasonic transducers 320. A plurality of electrode pads are also provided on the back surface of the base substrate 500 to be coupled to the electronic circuit modules. The electrode pads on the front surface of the base substrate 500 and the electrode pads on the back surface of the base substrate 500 are electrically coupled in one-to-one connection. In other words, the base substrate 500 respectively couples the ultrasonic transducers 320 to the FPCs 313 in the electronic circuit modules.

The pitches between the electrode pads on the base substrate 500 (hereinafter, wiring pitches) relate to the shape error when assembling an electronic circuit module. For instance, if the wiring pitch is determined to be 0.1 mm for the base substrate 500, a tolerance of the shape deviation when assembling one electronic circuit module needs to be 0.02 mm at most in order to arrange five electronic circuit modules without a gap GY. Furthermore, since the FPC folding error also needs to be taken into account as mentioned earlier, manufacturing costs may increase in order to satisfy the above tolerance range of the shape deviation.

In contrast, a gap GY may be provided between any two electronic circuit modules as in the present embodiment so that shape deviation in the dimension of the individual electronic circuit modules can be tolerated to some extent.

For instance, even if a wiring pitch of the base substrate 500 is determined to be 0.08 mm, which is below the aforementioned limit of 0.1 mm, the tolerance of the shape deviation is 0.04 mm because only the size of each individual electronic circuit module needs to be considered. The arrangement of gaps GY therefore can increase the tolerance range, in comparison with the structure without a gap GY. With the increased tolerance range, the manufacturing costs can be reduced.

Figure 9:
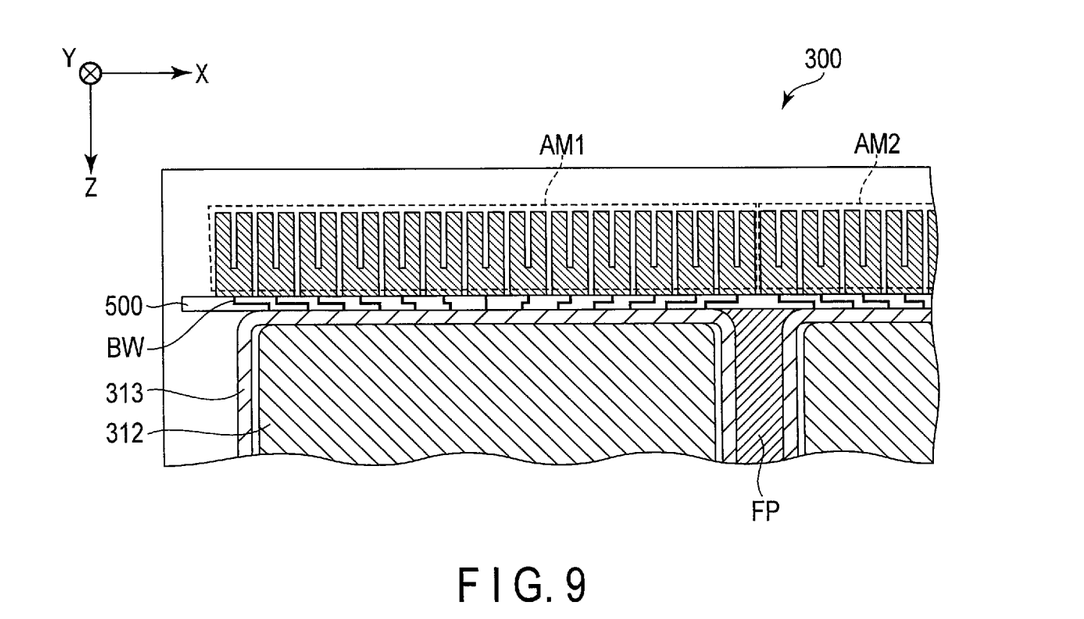
FIG. 9 is a diagram showing an exemplary wiring pattern on the base substrate of FIG. 8.

FIG. 9 is a diagram showing an exemplary wiring pattern on the base substrate of FIG. 8. Wirings BW that couple the electrode pads on the two surfaces of the base substrate 500 are provided in the base substrate 500. As illustrated in FIG. 9, the wiring pitch on the back surface of the base substrate 500 is smaller than the wiring pitch on the front surface of the base substrate 500. This is because of a gap GY provided between any two adjacent electronic circuit modules.

With the gap GY between the electronic circuit modules, each electronic circuit module can be individually arranged on the base substrate 500. If there is no gap GY, once an error occurs in the arrangement of an electronic circuit module that serves as a reference, errors may appear in all the other electronic circuit modules. In addition, if there are variations in the shapes of the electronic circuit modules, the variations in all the electronic circuit modules need to be taken into consideration at the time of assembly. For this reason, the electronic circuit modules need to be coupled together before being arranged on the base substrate 500. With gaps GY provided, the arrangement of only individual electronic circuit modules needs to be taken into consideration. Thus, the electronic circuit modules can be separately arranged as described earlier. Moreover, because the electronic circuit modules are independently provided, adverse effects can be reduced at the time of assembly even if there are variations in the shapes of the individual electronic circuit modules.

As discussed above, the ultrasonic probe according to the first embodiment includes a plurality of ultrasonic transducers equally spaced apart and aligned at least in one direction, a first substrate coupled to the ultrasonic transducers, and a plurality of electronic circuit modules provided at predetermined intervals on the first substrate and coupled to the first substrate. Thus, with a certain tolerance to manufacturing errors in the size of each electronic circuit module, the assembling precision of the ultrasonic probe can be improved.

Second Embodiment

In the first embodiment, gaps are provided between the electronic circuit modules. In the second embodiment, spacers are provided in these gaps.

Figure 10:
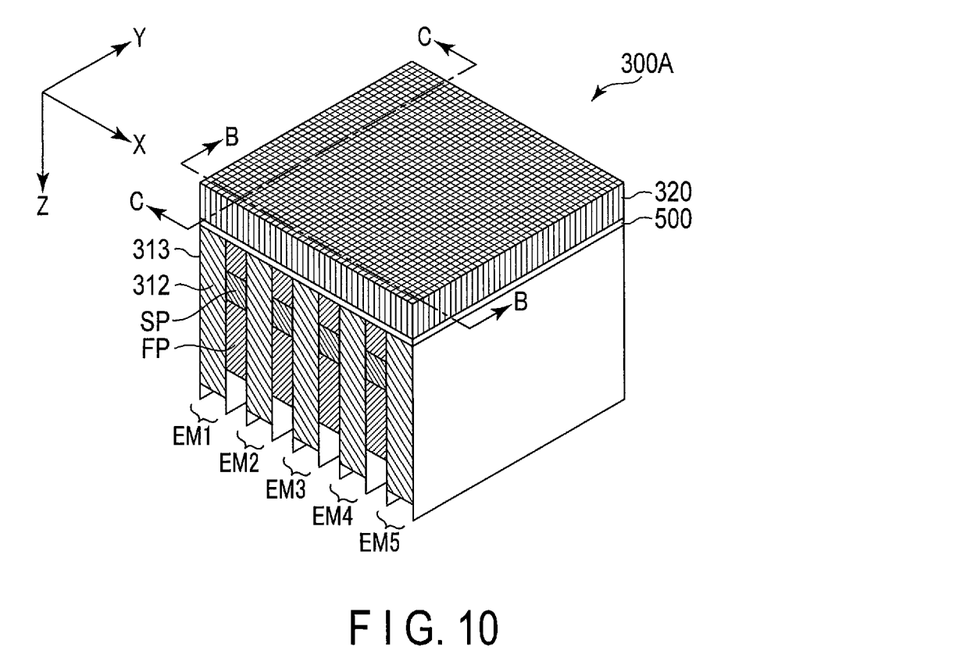
FIG. 10 is a perspective diagram for showing the configuration of a probe main body according to the second embodiment.

FIG. 10 is a perspective diagram showing the configuration of a probe main body according to the second embodiment. For instance, a probe main body 300A according to the second embodiment includes a plurality of ultrasonic transducers 320, the base substrate 500, and the electronic circuit modules EM1, EM2, EM3, EM4, and EM5, as illustrated in FIG. 10. A filler FP and a spacer SP are provided in a gap between the adjacent electronic circuit modules. Two spacers SP may be arranged in the azimuth direction; however, the number and shape of spacers are not limited thereto.

Figure 11:
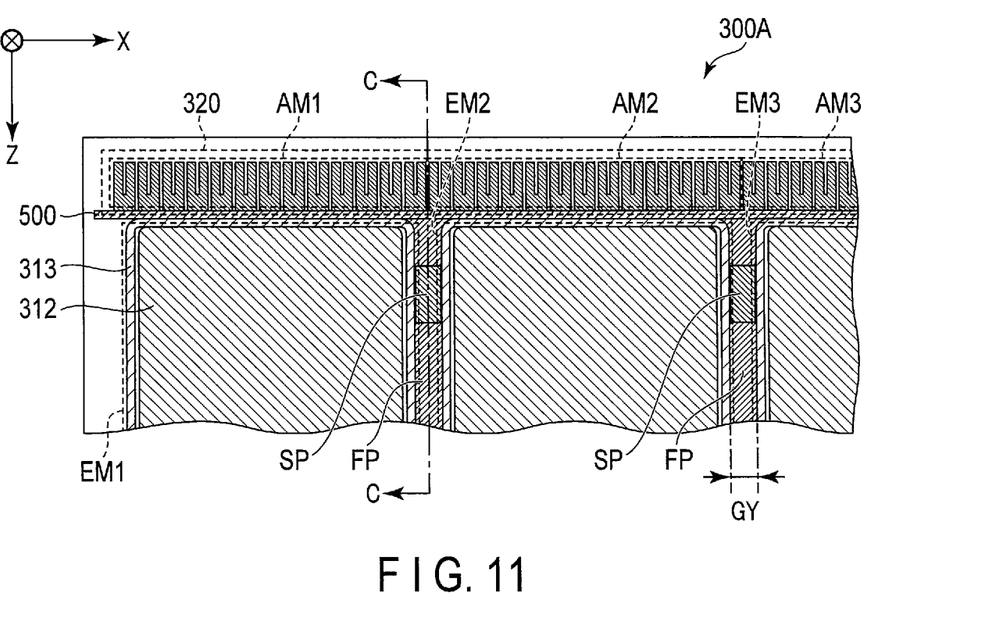
FIG. 11 is a cross-sectional view of the configuration of FIG. 10 taken along B-B in the Z-axis direction.

FIG. 11 is a cross-sectional view of the configuration of FIG. 10 taken along B-B in the Z-axis direction, where B-B is a line extending in the elevation direction (X-axis direction). The cross section of FIG. 11 is parallel to the XZ plane.

In FIG. 11, a filler FP and a spacer SP are provided in the gap between the electronic circuit module EM1 and electronic circuit module EM2. The spacer SP may have approximately the same width as the gap. Alternatively, the width of the spacer SP may be determined in consideration of the shape deviation of adjacent electronic circuit modules. In other words, the width of a gap may be predetermined, or may be determined by a spacer SP.

Figure 12:
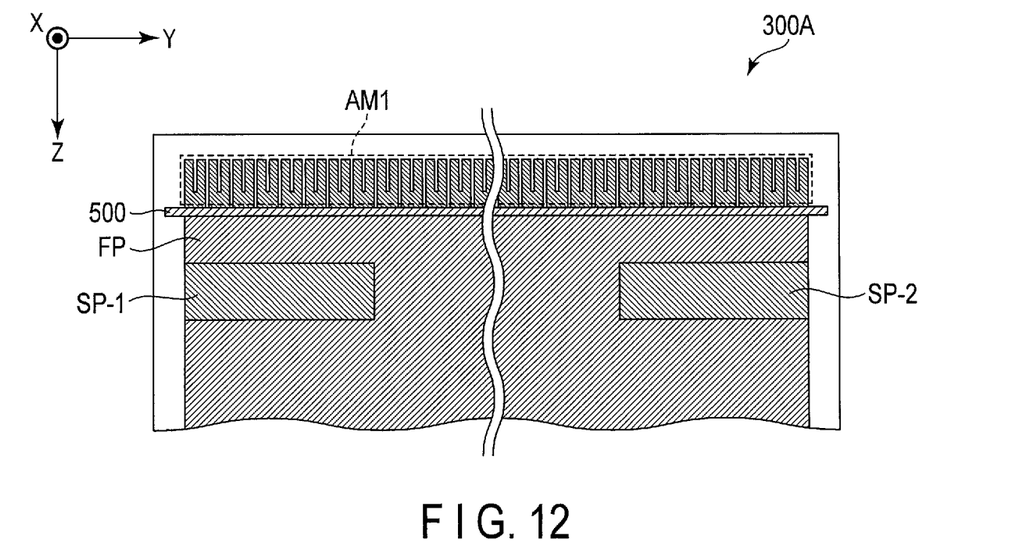
FIG. 12 is a cross-sectional view of the configuration of FIG. 10 taken along C-C in the Z-axis direction.

FIG. 12 is a cross-sectional view of the configuration of FIG. 10 taken along C-C in the Z-axis direction, where C-C in FIG. 10 is a line extending in the azimuth direction (Y-axis direction). The cross section of FIG. 12 is parallel to the YZ plane. In the cross-sectional view of FIG. 12, as indicated by the line C-C of FIG. 11, a filler FP and two spacers (spacers SP-1 and SP-2) are included.

By providing spacers in a gap between adjacent electronic circuit modules, the same assembling method as the conventional technique can be adopted for the probe main body 300A, without losing any assembling precision. In particular, with this assembling method, the electronic circuit module EM1 is initially aligned with the base substrate 500, a spacer SP is positioned for the aligned electronic circuit module EM1, and the electronic circuit module EM2 is positioned in such a manner as to sandwich the spacer SP with the electronic circuit module EM1. After sandwiching the spacer SP between the two electronic circuit modules, the gap is filled with the filler FP. Other spacers and electronic circuit modules are positioned in a similar manner, and each time a new gap is produced, the gap is filled with a filler. In this manner, after the alignment of a reference electronic circuit module, alignment for other electronic circuit modules can be omitted.

The reference electronic circuit module is not limited to the one on an edge portion of the base substrate (e.g., electronic circuit module EM1 or electronic circuit module EM5), and it may be an electronic circuit module in the center area of the base substrate (e.g., electronic circuit module EM3).

As discussed above, the ultrasonic probe according to the second embodiment includes a plurality of ultrasonic transducers equally spaced and aligned at least in one direction, a first substrate coupled to the ultrasonic transducers, and a plurality of electronic circuit modules provided at predetermined intervals on the first substrate and coupled to the first substrate. Furthermore, the ultrasonic probe includes a spacer having the same width as the length of the interval and arranged between the electronic circuit modules. The ultrasonic probe, in which the distance between two electronic circuit modules can be adjusted by the spacer, can be easily assembled in the production.

Third Embodiment

In the first and second embodiments, coupling of the electronic circuit modules in the elevation direction has been explained. In the third embodiment, coupling of electronic circuit modules in the azimuth direction will be explained.

Unlike the first and second embodiments, the axis along the azimuth direction will be referred to as an X-axis, and the axis along the elevation direction will be referred to as a Y-axis, which is orthogonal to the X-axis, in the third embodiment.

Figure 13:
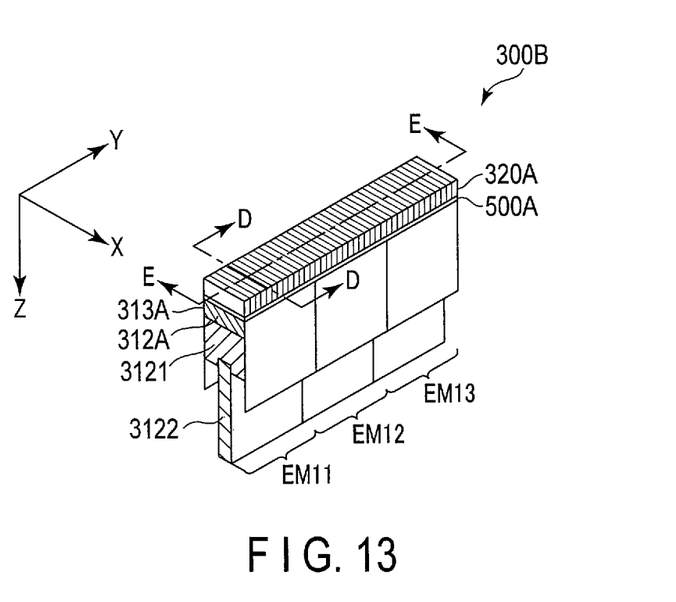
FIG. 13 is a perspective diagram of the configuration of a probe main body according to the third embodiment.

FIG. 13 is a perspective diagram showing the configuration of the probe main body according to the third embodiment. The probe main body 300B according to the third embodiment includes a plurality of ultrasonic transducers 320A, a base substrate 500A, and electronic circuit modules EM11, EM12, and EM13, as illustrated in FIG. 13.

The ultrasonic transducers 320A are arranged at regular intervals in a one-dimensional direction (Y-axis direction in FIG. 13). In the same manner as in the first embodiment, the transmission/reception IC 311 sets a delay amount for each element so that the ultrasonic transducers 320A transmit an ultrasound wave generated based on the drive signal to a subject P at a timing corresponding to the delay amount. The ultrasonic transducers 320A may be further divided in the X-axis direction.

The base substrate 500A may be an FPC or the like. The base substrate 500A may be a flexible wiring board. The base substrate 500A is provided between the ultrasonic transducers 320A and the electronic circuit modules EM11, EM12, and EM13. The base substrate 500A supports the ultrasonic transducers 320A. The base substrate 500A is divided into structures corresponding to the electronic circuit modules EM11, EM12, and EM13. The base substrate 500A electrically couples the ultrasonic transducers 320A to the electronic circuit modules EM11, EM12, and EM13 for each module.

Each of the electronic circuit modules EM11, EM12, and EM13 includes a backing material 312A, an FPC 313A, a metallic member 3121, and a support member 3122. The physical configuration of an electronic circuit module will be described below. The FPC 313A may also be referred to as a flexible wiring board.

Figure 14:
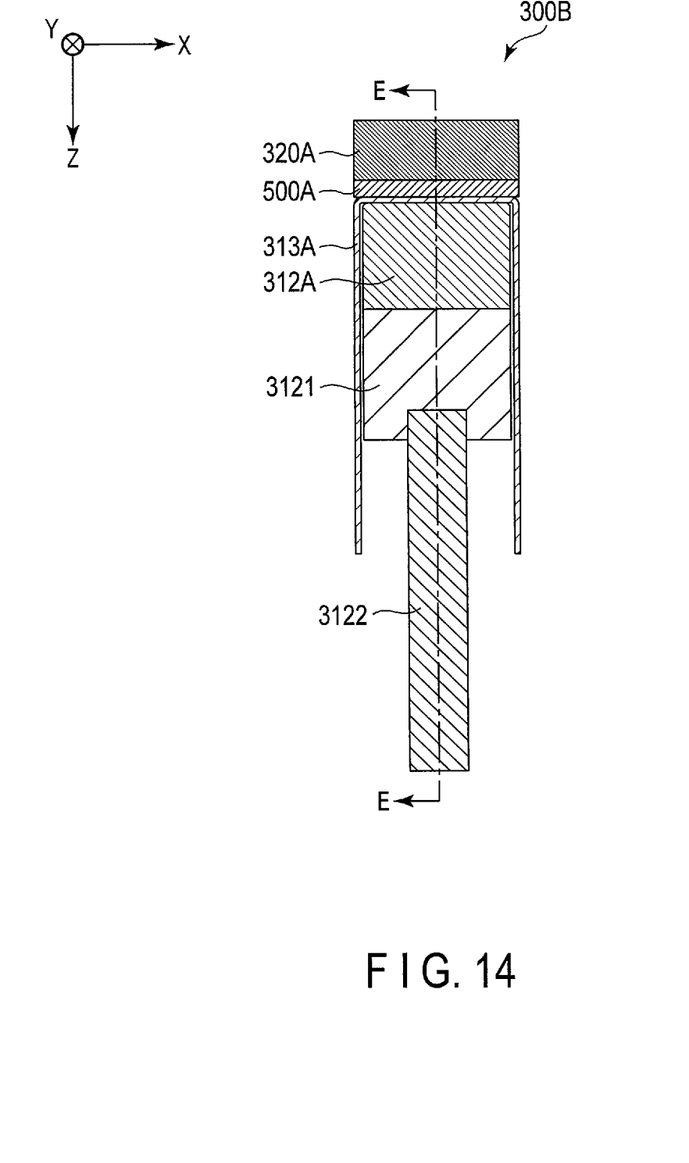
FIG. 14 is a cross-sectional view of the configuration of FIG. 13 taken along D-D in the Z-axis direction.

FIG. 14 is a cross-sectional view of the configuration of FIG. 13 taken along D-D in the Z-axis direction, where D-D is a line extending in the azimuth direction (X-axis direction). The cross section of FIG. 14 is parallel to the XZ plane. FIG. 14 shows a cross section of the electronic circuit module EM11; other electronic circuit modules have similar cross sections.

The backing material 312A is configured to prevent ultrasound waves from propagating backward (i.e., in the positive direction of the Z-axis) with respect to the acoustic radiation direction of the ultrasonic transducers 320A. The width of the backing material 312A in the azimuth direction (X-axis direction) may be determined in accordance with the width of the ultrasonic transducers 320A in the azimuth direction. Furthermore, the length of the backing material 312A in the elevation direction (Y-axis direction) may be determined in accordance with the length of an electronic circuit module, or of a module including ultrasonic transducers in the elevation direction. The surface of the backing material 312A is partially covered by the FPC 313A.

The FPC 313A is adhered to part of the surface of the backing material 312A. In particular, the FPC 313A is folded in such a manner as to be approximately in contact with the surface (first surface) of the backing material 312A on the negative direction side of the Z-axis, the surface thereof on the positive direction side of the X-axis, and the surface thereof on the negative direction side of the X-axis, and the FPC 313A is adhered at least to the first surface. The surface of the backing material 312A on the negative direction side of the Z-axis is parallel to the base substrate 500A. As a result, the FPC 313A has a two-layer structure with respect to the direction of the X-axis.

The metallic member 3121 supports the backing material 312A. In particular, the metallic member 3121 is in contact with and adhered to the surface of the backing material 312A on the positive direction side of the Z-axis. The opposite surface of the metallic member 3121 (i.e., the surface on the positive direction side of the Z-axis) with respect to the surface adhered to the backing material 312A is shaped so as to hold and support the support member 3122 (into a groove, for example). Alternatively, the metallic member 3121 may have a projection in place of a groove. The groove may also be referred to as a concavity.

The support member 3122 is fixed in the groove of the metallic member 3121 and supports the metallic member 3121. For the support member 3122, a metal or hard resin may be used. The support member 3122 is fixed on the probe main body 300 with a not-shown fixation member so as to securely hold the metallic member 3121. The shape of the support member 3122 is not limited to a rectangular column having a surface that can be engaged with the bottom surface of the metallic member 3121. The support member 3122 may have a shape with a protrusion that can be engaged with the bottom surface and groove of the metallic member 3121. When a protrusion is formed in the metallic member 3121, the support member 3122 may have a shape with a concavity that can be engaged with the protrusion.

Figure 15:
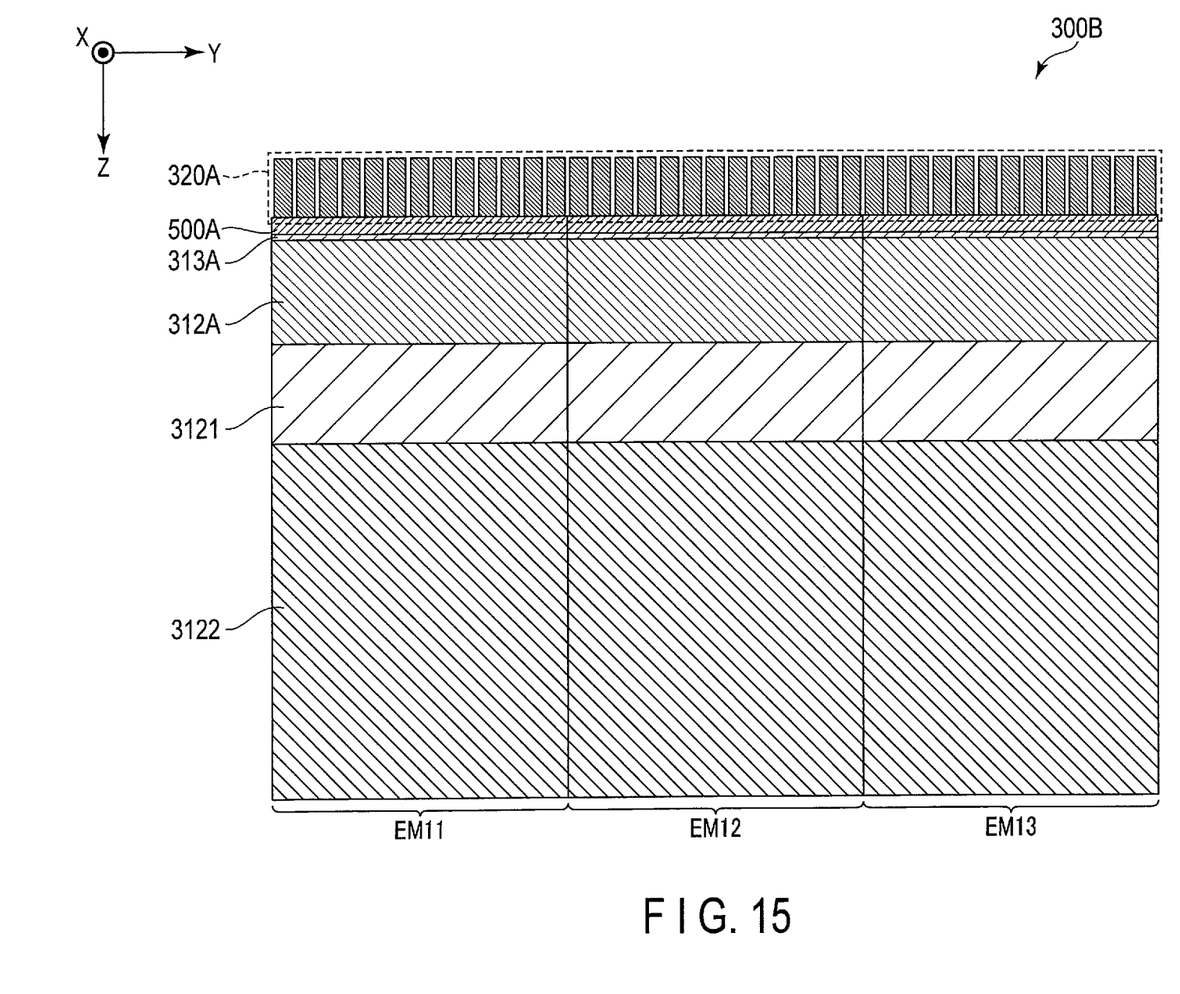
FIG. 15 is a cross-sectional view of the configuration of FIG. 13 taken along E-E in the Z-axis direction.

FIG. 15 is a cross-sectional view of the configuration of FIG. 13 taken along E-E in the Z-axis direction, where E-E of FIG. 13 is a line extending in the elevation direction (Y-axis direction). The cross section of FIG. 15 is parallel to the YZ plane. As indicated by the line E-E in FIG. 14, this cross section includes a groove in the metallic member 3121.

In the probe main body 300B according to the third embodiment, a module is constituted by ultrasonic transducers, a base substrate, and an electronic circuit module, as illustrated in FIG. 15. In particular, the probe main body 300B is constituted by three modules, namely a first module including the electronic circuit module EM11, a second module including the electronic circuit module EM12, and a third module including the electronic circuit module EM13. With the probe main body constituted by a plurality of modules, yields can be improved in the assembling process of the probe main body, in comparison with a probe main body constituted by a single module. The number of modules is not limited to three.

As described above, the ultrasonic probe according to the third embodiment is formed by connecting modules of the same type. Each module includes a plurality of ultrasonic transducers equally spaced and aligned at least in one direction, a first substrate coupled to the ultrasonic transducers, an acoustic load member, a second substrate folded so as to be in contact with three surfaces of the acoustic load member, adhered at least to a first surface of the three surfaces and brought into contact with the first substrate, and a metallic member adhered to an opposite surface of the acoustic load member with respect to the first surface. The metallic member has a shape such that it can hold and support a support member on the opposite surface with respect to the surface to which the acoustic load member is adhered. Such an ultrasonic probe can securely support the ultrasonic transducers, first substrate, acoustic load member, and second substrate with the metallic member, thereby enhancing the strength of a module.

The term "processor" used in the above description may denote a circuit such as a central processing unit (CPU), a graphics processing unit (GPU), an application specific integrated circuit (ASIC), and a programmable logic device (e.g., simple programmable logic device (SPLD), complex programmable logic device (CPLD), or field programmable gate array (FPGA)). The processor realizes functions by reading and executing a program stored in the memory circuitry. The processors according to the embodiments are not limited to a single circuit for each processor, but may be configured as a process by combining different independent circuits to realize the functions. Furthermore, the structural components illustrated in FIG. 1 may be integrated into one processor to realize their functions.

According to at least one embodiment described above, the precision of assembly in the manufacturing process of ultrasonic probes can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic probe, comprising:
   a plurality of ultrasonic transducers equally spaced and aligned at least in one direction;
   a first substrate to which the ultrasonic transducers are coupled, the first substrate being a non-divided structure; and
   a plurality of electronic circuit modules arranged spaced apart from each other by a predetermined distance on the first substrate and coupled to the first substrate, wherein
   each of the electronic circuit modules includes:
      an acoustic load member; and
      a second substrate folded in such a manner as to be in contact with three surfaces of the acoustic load member, adhered at least to a first surface of the three surfaces, and coupled to the first substrate, and
   the first surface is parallel to the first substrate.

2. The ultrasonic probe according to claim 1, further comprising:
   a filler provided between any adjacent two of the electronic circuit modules.

3. The ultrasonic probe according to claim 2, wherein the filler is at least one of (i) all or a portion of materials of an acoustic load member and (ii) an epoxy resin.

4. The ultrasonic probe according to claim 1, further comprising:
   a spacer provided between any adjacent two of the electronic circuit modules and having a width that is the same length as the predetermined distance.

5. The ultrasonic probe according to claim 1, wherein each of the electronic circuit modules includes a metallic member adhered to a surface of the acoustic load member opposite the first surface, and the metallic member has a surface opposite the surface to which the acoustic load member is adhered, the opposite surface having a shape for holding and supporting a support member.

6. The ultrasonic probe according to claim 5, wherein the metallic member has, as the shape, at least a concavity or a protrusion.

7. The ultrasonic probe according to claim 1, wherein the electronic circuit modules are coupled to the first substrate in such a manner that one of the folded surfaces of the second substrate of one electronic circuit module is adjacent to one of the folded surfaces of the second substrate of an adjacent electronic circuit module.

8. An ultrasonic probe constituted by coupling modules of a same type to each other,
   each of the modules comprising:
      a plurality of ultrasonic transducers equally spaced and aligned at least in one direction;
      a first substrate to which the ultrasonic transducers are coupled;
      an acoustic load member;
      a second substrate folded in such a manner as to be in contact with three surfaces of the acoustic load member, adhered at least to a first surface of the three surfaces, and coupled to the first substrate; and
      a metallic member adhered to a surface of the acoustic load member opposite the first surface, wherein
   the metallic member has a surface opposite the surface to which the acoustic load member is adhered, the opposite surface having a shape for holding and supporting a support member.

9. The ultrasonic probe according to claim 8, wherein the metallic member has, as the shape, at least a concavity or a protrusion.

10. An ultrasonic probe, comprising:
    a plurality of ultrasonic transducers equally spaced and aligned at least in one direction;
    a first substrate to which the ultrasonic transducers are coupled; and
    a plurality of electronic circuit modules provided at predetermined intervals on the first substrate and coupled to the first substrate, wherein
    each of the electronic circuit modules includes:
       an acoustic load member; and
       a second substrate folded in such a manner as to be in contact with three surfaces of the acoustic load member, adhered at least to a first surface of the three surfaces, and coupled to the first substrate,
    the first surface is parallel to the first substrate, and
    a metallic member adhered to a surface of the acoustic load member opposite the first surface, the metallic member having a surface opposite the surface to which the acoustic load member is adhered and the opposite surface having a shape for holding and supporting a support member.

* * * * *